US006668833B2

(12) United States Patent
Rhee

(10) Patent No.: US 6,668,833 B2
(45) Date of Patent: Dec. 30, 2003

(54) BIRTHING AID

(75) Inventor: Ju Chul Rhee, 1818 N. Orange Grove, #302, Upland, CA (US) 91767

(73) Assignee: Ju Chul Rhee, Upland, CA (US)

( * ) Notice: Subject to any disclaimer, the term of this patent is extended or adjusted under 35 U.S.C. 154(b) by 540 days.

(21) Appl. No.: 09/746,912

(22) Filed: Dec. 26, 2000

(65) Prior Publication Data

US 2001/0008957 A1 Jul. 19, 2001

Related U.S. Application Data

(63) Continuation-in-part of application No. 09/407,028, filed on Sep. 27, 1999.

(51) Int. Cl.$^7$ .............................................. A61G 15/00
(52) U.S. Cl. ........................................ 128/845; 601/45
(58) Field of Search ...................... 601/45, 152; 5/602, 5/651; 128/845; 606/119; 600/588

(56) References Cited

U.S. PATENT DOCUMENTS

| | | | | |
|---|---|---|---|---|
| 6,385 A | * | 8/1849 | Pollard | |
| 7,590 A | * | 8/1850 | Blood | |
| 10,649 A | * | 3/1854 | Daniels | |
| 68,521 A | * | 9/1867 | Manley | |
| 667,621 A | * | 2/1901 | Fleming | |
| 778,644 A | * | 12/1904 | Easterly | |
| 800,071 A | * | 9/1905 | Cheatham | |
| 846,648 A | * | 3/1907 | Crume | |
| 2,597,637 A | * | 5/1952 | Heidenwolf | |
| 4,180,062 A | * | 12/1979 | Alberti et al. | 600/511 |
| 5,287,860 A | * | 2/1994 | Owens | 128/851 |
| 5,895,366 A | * | 4/1999 | Bzoch | |

\* cited by examiner

Primary Examiner—Nicholas D. Lucchesi
Assistant Examiner—Lalita M Hamilton
(74) Attorney, Agent, or Firm—Knobbe, Martens, Olson & Bear, LLP

(57) ABSTRACT

A birthing aid comprised of a rectangularly shaped compliant band dimensioned to be wrapped around the shin or thigh of a patient who is engaged in the birthing process. A compliant handle is attached to the outer surface of the band and positioned so that when a birthing aid is mounted on each leg, the patient may comfortably grasp the handles. A fastening system such as Velcro® is attached to each surface of the band in order fix each mounted band in place. Alternatively, the bands may be held in place by a quick-drying adhesive or instant glue. Other embodiments include a tapered cylinder, a series of loops, and a boot. These are all comprised of a compliant material. All have handles. The patient uses the handles to draw her legs toward her, thus assuming the preferred drawn-up legs position.

5 Claims, 4 Drawing Sheets

Fig. 11
Fig. 10
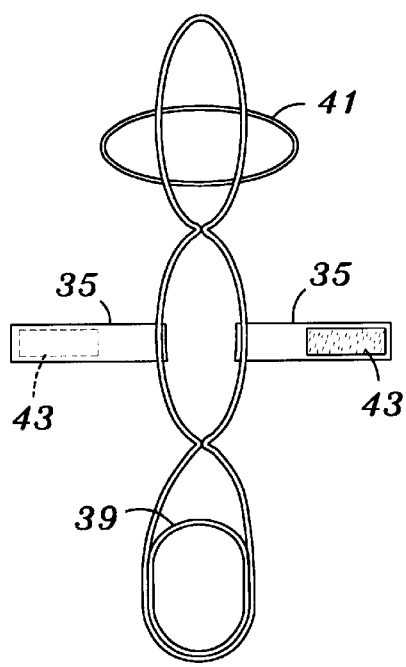
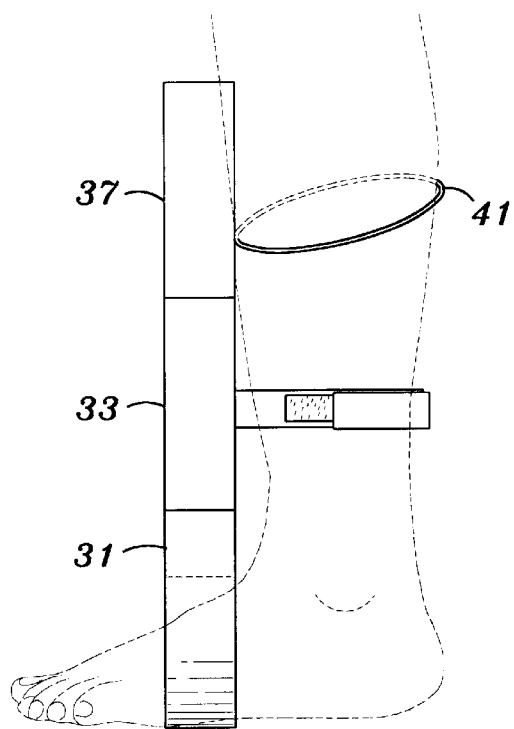
Fig. 12
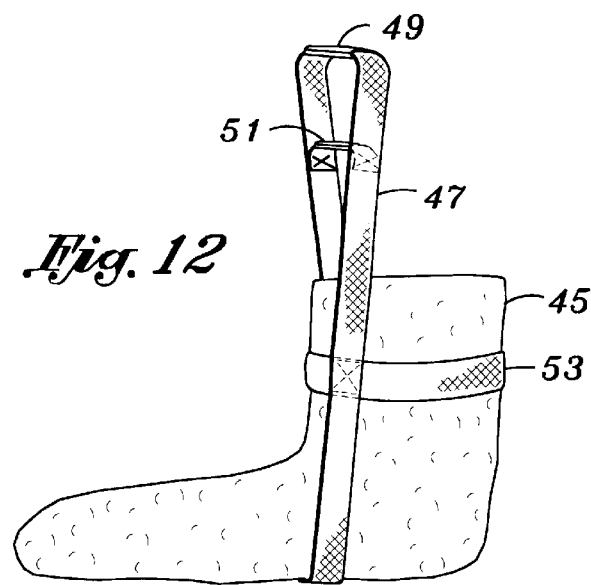

BIRTHING AID

This is a Continuation-In-Part of Application Ser. No. 09/407,028 filed Sep. 27, 1999

BACKGROUND OF THE INVENTION

1. Field of the Invention

This invention relates generally to birthing aids and more specifically to a birthing aid that permits the patient to assume a more comfortable position during the birthing process and become productively engaged in the most painful and difficult stage of the birthing process.

2. Description of the Prior Art

U.S. Pat. No. 4,703,975 shows a birthing chair whereby during delivery the patient may grasp handgrips that are an integral part of the arm of the chair.

U.S. Pat. No. Des. 336,578 shows a handgrip for a birthing bed.

U.S. Pat. No. Des. 353,460 shows a birthing chair equipped with gripping handles.

Accordingly, one object and advantage of the present invention is to provide means by which a patient, who is ready to push during labor, may assume a more efficient position while delivering a baby.

Another object and advantage of the present invention is that the patient can maintain the more efficient position without assistance.

Another object and advantage of this invention is that the birthing aid may be configured and placed in use in accordance with the unique anatomical shape of the individual patient.

Further objects and advantages of this invention will become apparent from consideration of the drawings and ensuing description of it.

SUMMARY OF THE INVENTION

While enduring childbirth, there is a natural tendency for a patient who is experiencing an uncontrollable urge to push, to assume a supine or semi-supine position. This enables her to hold her head up, curl her spine, and draw her legs toward her body. Patients who have had a regional anesthesia and who consequently do not experience the urge to push still have to expel the baby from the birth canal. These patients may also assume the semi-supine position. In this manner, pressure from the contractions the patient is experiencing is most efficiently transmitted to the birth canal. To assume this attitude, the patient uses her hands to draw her legs as close to her body as possible, subject to the restraint imposed by her protuberant abdomen. During the exhausting childbirth process, the patient often has difficulty in maintaining a grip on her legs. In some instances, an attendant or relative may offer assistance by holding the patient's legs in the most favorable position.

The present invention, henceforth called a birthing aid, comprises a rectangularly shaped band of compliant material dimensioned to overlap the shin, or alternatively, the thigh area of the patient's leg. The opposing side of each end of the band is terminated with a strip of complimentary hook-and-pile material such as Velcro® that secures the mounted band in place. An alternate disposable embodiment utilizes a quick-drying adhesive or instant glue to secure the mounted band in place.

The band further includes a grip comprised of a suitably dimensioned strip of compliant material secured at each end by attaching means to the outer surface of the mounted band and positioned so that when a birthing aid is wrapped about each shin or thigh of the patient, the grips are optimally located for reach by that particular patient, thereby providing her with a secure and tractable purchase.

In this manner, the improved hold afforded to the patient by the birthing aid will allow her to comfortably and independently maintain the preferred drawn-up leg position during the childbirth process.

BRIEF DESCRIPTION OF THE DRAWINGS

FIGS. 10 and 11 show an alternate embodiment in which the compliant band has been configured to form three loops, a bottom loop 31 that functions as a stirrup and contains a reinforcing band 39. A middle loop 33 to which attaching strips 35 are included, and a top loop 37 that functions as a handle. The top loop further includes a restraining cord 41. The attaching strips show hook and pile fastening material 43. In an alternate disposable embodiment, a quick-dry adhesive or instant glue replaces the fastening material.

FIG. 12 shows an alternate embodiment of the birthing aid whereby the compliant material has been formed into the shape of a boot 45. Further included is a looped band 47 that passes under the arch of the boot and terminates in a handle 49. An additional handle 51 is provided to ensure proper reach. The looped band is secured to the boot by the attaching band 53.

DESCRIPTION OF THE PREFERRED EMBODIMENT

Figure 1:
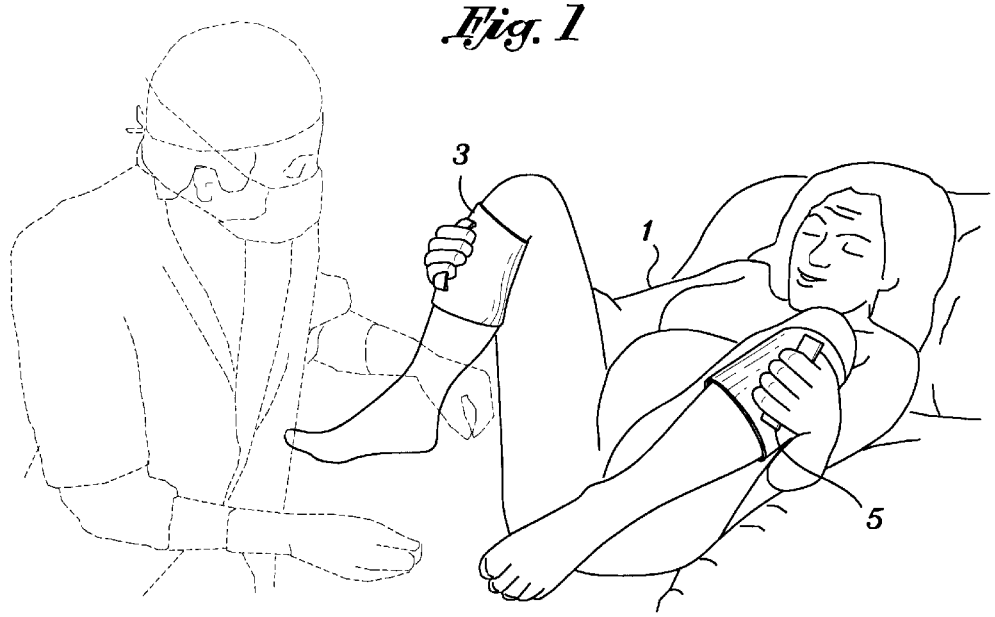
FIG. 1 shows a patient 1 grasping the handles 5 of the birthing aid to assist her in drawing up her legs as far as comfortably possible. This figure further depicts the location of the compliant band 3 as it is wrapped about the patients shin area.

The birthing aid is comprised of a band of rectangularly shaped compliant material dimensioned to be wrapped around the shin, or alternatively, the thigh area of a patient who is being prepared to enter the birthing process. Further included is a compliant handle attached to the band in such a manner as to provide a comfortable position for the patient. FIG. 1 is a depiction of the birthing aid in use as the patient grasps the handles 5 of the device. Here, the handles are shown to be composed of a compliant material. In this particular instance, the compliant bands 3 are shown wrapped around the shin area of the patient and held in place by a fastening system such as Velcro®. In an alternate, disposable embodiment, the Velcro® fastening system is replaced by a quick-drying adhesive or instant glue. The anatomical composition of some patients may require that the compliant band be wrapped around the thigh area.

Figure 2:
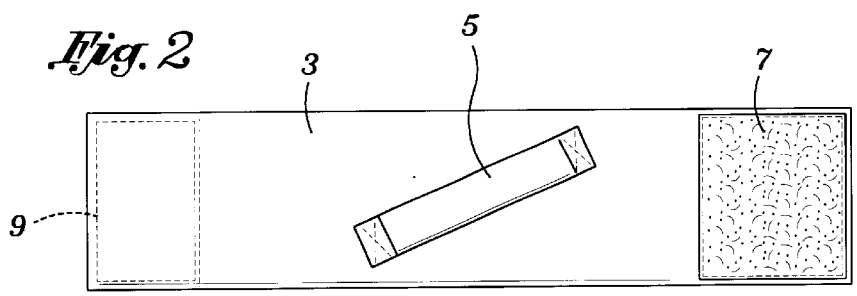
FIG. 2 shows the outer surface of the birthing aid in which the handle 5 has been attached to the band 3 at an angle that has been determined to be most convenient for the patient. The angle may be clearly seen in FIG. 1. Also shown is the pile material 7 used to secure the wrapped band in place.
Figure 3:
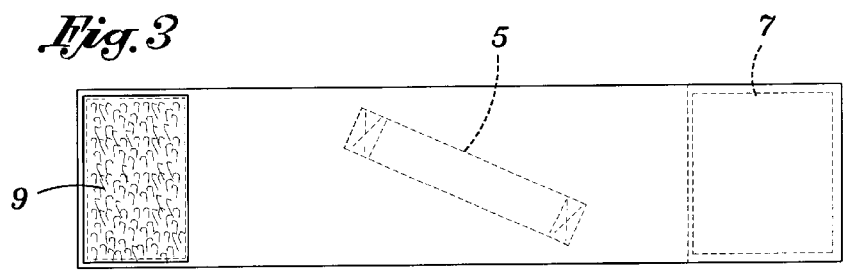
FIG. 3 shows the inner surface of the birthing aid where the hook material 9 that engages the pile material 7 of FIG. 2 may be seen.

FIG. 2 shows the outer surface of the birthing aid. Here, the handle has been attached to the band at an angle that presents the most comfortable grip to the patient. A strip of pile material 7 is shown attached on the outer surface of the band 3. A complimentary strip of hook material 9 is attached on the inner surface of the band as shown in FIG. 3. Thus, when the band is wrapped around the shin or thigh area, the hook-and-pile fastening system combines, holding the birthing aid in place. So positioned, the patient may then grip the handles and pull her legs toward her body.

Figure 4:
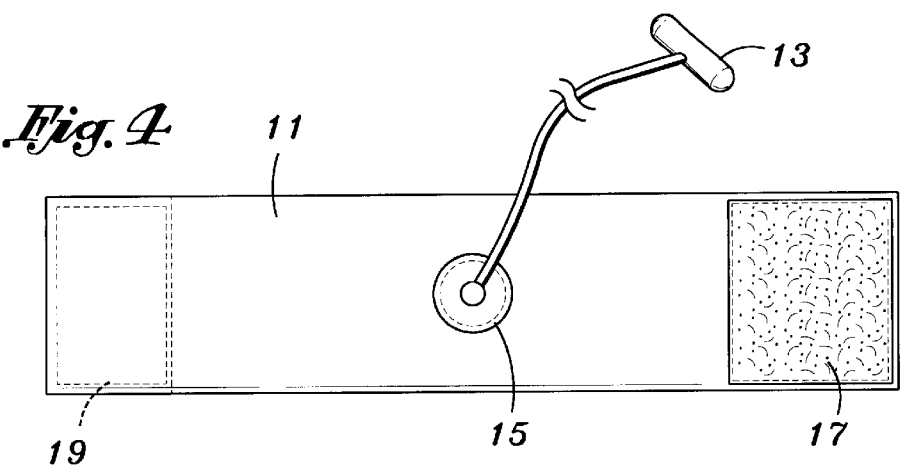
FIG. 4 shows the outer surface of an alternate embodiment where the compliant handle 5 of FIG. 2 has been replaced by a rigid handle 13 that is connected by a thong to an attaching ring 15 mounted on the compliant band 11. Also shown is the pile material 17 used to secure the wrapped band in place.
Figure 5:
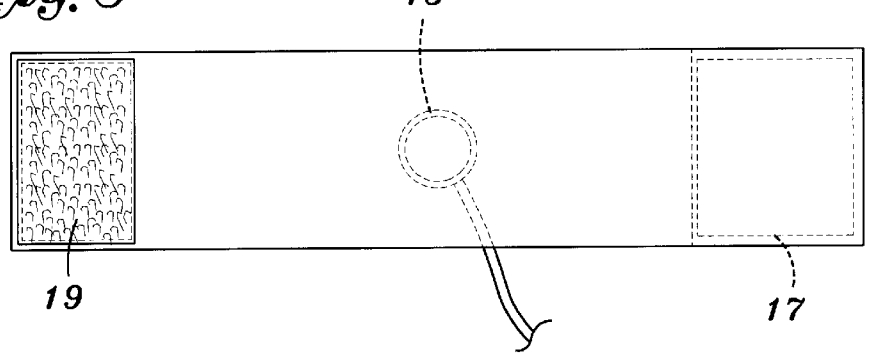
FIG. 5 shows the inner surface of the birthing aid where the hook material 19 that engages the pile material of FIG. 4 may be seen.

A large-framed or portly patient may not be physically able to grasp the compliant handles. Consequently, an alternate embodiment is shown in FIG. 4. Here, a rigid handle 13 has replaced the compliant handle. The handle is attached to a thong, which in turn is fixed to the band 11 with an attaching ring 15. The thong is dimensioned so that when the birthing aid is mounted, the patient may comfortably reach and grip the rigid handle. Again, the band terminates in a strip of pile material 17 that is complimented by a strip of hook material 19 as shown in FIG. 5. The birthing aid is used in the same manner: The band is wrapped around the shin or thigh area. The hook-and-pile or adhesive fastening system combines, holding the birthing aid in place. The patient then grips the rigid handles and pulls her legs toward her body, thus assuming the preferred drawn-up leg position.

Figure 6:
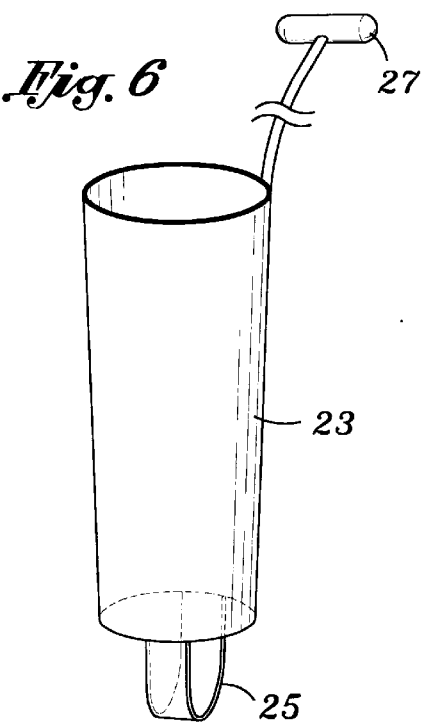
FIG. 6 shows an alternate embodiment of the birthing aid whereby the compliant band has been pre-formed into a tapered cylindrical shape 23. A thong attaches a handle 27 to the outer surface of the cylinder at a location most convenient for the patient. A restraining stirrup 25 may also be seen.

Another embodiment is shown in FIG. 6. Here, the birthing aid is cylindrically shaped and tapered. The cylinder 23 is comprised of a compliant material. The length of the cylinder is dimensioned to span the distance between the patient's ankle and her knee. A handle 27 that is attached to the cylinder by a thong provides a grip for the patient. The narrow end of the cylinder terminates in a restraining stirrup 25 that is comprised of a compliant material. In use, the wide end of the cylinder is slipped over one of the patient's legs and pulled up to her knee. So mounted, the stirrup abuts against the patient's instep, fixing the birthing aid in place. This procedure is repeated for the other leg. The patient may now grip the handles and pull her legs toward her, thus assuming the preferred drawn-up leg position.

Figure 8:
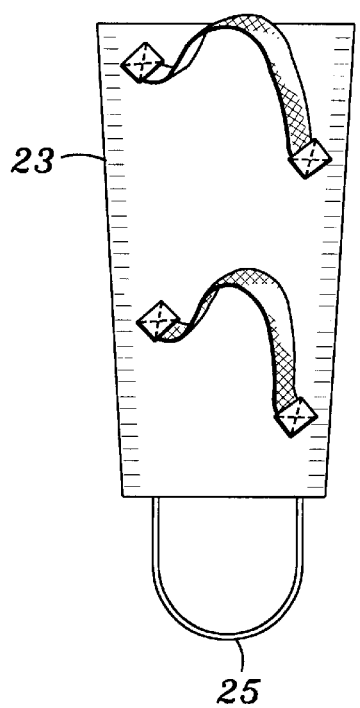
FIGS. 7, 8, and 9 show the cylinder of FIG. 6 where the rigid handle has been replaced by two compliant handles 29. The handles are optimally located for reach by the patient.
Figure 7:
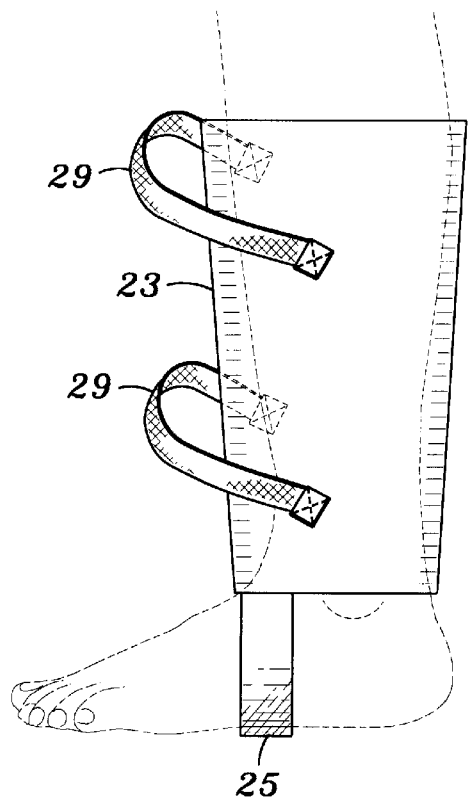
Figure 9:
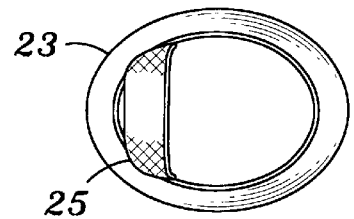

Another embodiment is shown in FIGS. 7, 8, and 9. Again, the birthing aid is cylindrically shaped and tapered as in FIG. 6. The cylinder 23 is composed of a compliant material. The length of the cylinder is dimensioned to span the distance between the patient's ankle and her knee. The narrow end of the cylinder terminates in a restraining stirrup 25 that is comprised of a compliant material. A compliant handle 29 is positioned at each end of the tapered cylinder to provide an optimal grip for the patient. The handles are mounted at an angle relative to the axis of the cylinder. Accordingly, two distinct birthing aids are required, one for the right leg and one for the left leg. In use, the wide end of the cylinder is slipped over one of the patient's legs and pulled up to her knee. So mounted, the stirrup abuts against the patient's instep, fixing the birthing aid in place. This procedure is repeated for the other leg. The patient may now grip the handles that are most comfortable for her and pull her legs toward her, thus assuming the preferred drawn-up leg position.

Another embodiment is shown in FIGS. 10 and 11. Here, the birthing aid is comprised of a series of three sequentially attached loops 31 33 and 37. Each loop is comprised of a compliant material and the three loops in series are dimensioned to span the distance between the patient's instep and her knee. The lower loop 31 functions as a restraining stirrup. The lower loop further includes a band 39 formed of an elastic material to secure the patient's foot in place within the lower loop. The middle loop 33, which functions as a handle, includes attaching strips 35 that are dimensioned to wrap around the patient's calf. The attaching strips further include hook and pile fastening system 43. In an alternate disposable embodiment, a quick-dry adhesive or instant glue replaces the hook and pile system. The top loop 37, which also functions as a handle, is positioned in place by an elastic restraining cord 41 that wraps around the patient's upper calf. The restraining cord ensures that the handle is positioned so that the patient may readily grip it. In use, a birthing aid is mounted on each of the patient's legs. The patient may then grip the handle most convenient for her and pull her legs toward her, thus assuming the preferred drawn-up leg position.

Another embodiment is shown in FIG. 12. Here, the birthing aid is comprised of a compliant material that has been formed into the shape of a boot 45. Further included is a looped band 47 that passes under the arch of the boot to form a stirrup. The loop terminates in a handle 49. An additional handle 51 is provided to ensure proper reach. The looped band is secured to the boot by the attaching band 57. In use, a boot is placed on each foot. The patient may then grip the most convenient handle and pull her legs toward her body, thus assuming the preferred drawn-up leg position.

Based on the description of FIGS. 1 through 12, it can be seen that the present invention provides the assistance a patient needs to comfortably maintain the preferred legs drawn-up position while pushing during the second stage of labor that will allow her to more efficiently deliver her baby.

Although the description above contains many specifications, these should not be construed as limiting the scope of the invention, but as merely providing illustrations of some of the presently preferred embodiments of the invention.

What is claimed is:

1. A method of assisting a childbirth effort of a pregnant woman, the method comprising:

grasping a first handle having two ends, said first handle being attached to a first band of material, wherein said first band of material is attached by fastening means to the woman's left leg below the left knee said left leg having a lateral aspect and a medial aspect, wherein each of the two ends of the first handle are attached to said first band of material at locations that are at the lateral aspect of the woman's left leg;

grasping a second handle having two ends, said second handle being attached to a second band of material, wherein said second band of material is attached by fastening means to a woman's right leg below the right knee said right leg having a lateral aspect and a medial aspect, wherein each of the two ends of the first handle are attached to said first band of material at locations that are at the lateral aspect of the woman's right leg; and pulling said first and second handles toward the woman's shoulders, thereby pulling said left and right knees toward the woman's shoulders;

wherein the woman is in a second stage of labor.

2. The method of claim 1, the first and second bands comprise compliant material.

3. The method of claim 1, wherein the first and second bands comprise fastening means for securing the first and second bands in place when wrapped about the lower legs of the patient.

4. The method of claim 1, wherein the fastening means comprises a hook and pile system.

5. The method of claim 1, wherein one of the handles is positioned on an outer surface of one of the bands so as to be easily grasped by the patient.

* * * * *